United States Patent [19]
Willert et al.

[11] Patent Number: 5,171,287
[45] Date of Patent: Dec. 15, 1992

[54] PLASTIC ACETABULUM

[75] Inventors: Hans-Georg Willert, Gottingen, Fed. Rep. of Germany; Rudolf Koch, Berlingen; Maya Burgi, Raterschen, both of Switzerland

[73] Assignee: Sulzer Brothers Limited, Winterthur, Switzerland

[21] Appl. No.: 662,234

[22] Filed: Feb. 28, 1991

[30] Foreign Application Priority Data

Mar. 13, 1990 [CH] Switzerland ............... 00799/90

[51] Int. Cl.$^5$ .................................. A61F 2/34
[52] U.S. Cl. .................................. 623/22
[58] Field of Search .......................... 623/22

[56] References Cited

U.S. PATENT DOCUMENTS

| | | | |
|---|---|---|---|
| 3,740,769 | 6/1973 | Haboush | 3/1 |
| 3,806,960 | 4/1974 | Weber | 3/1 |
| 4,531,243 | 7/1985 | Weber et al. | 623/22 |
| 4,871,368 | 10/1989 | Wagner | 623/22 |
| 5,021,063 | 6/1991 | Täger | 623/22 |

FOREIGN PATENT DOCUMENTS

| | | | |
|---|---|---|---|
| 0340175 | 11/1989 | European Pat. Off. | 623/22 |
| 2807289 | 2/1978 | Fed. Rep. of Germany | 623/22 |
| 2134170 | 12/1972 | France . | |
| 2250279 | 5/1975 | France . | |
| 0649913 | 6/1985 | Switzerland . | |
| 0666611 | 8/1988 | Switzerland . | |
| 2154141 | 9/1985 | United Kingdom | 623/22 |

Primary Examiner—David Isabella
Assistant Examiner—Debra S. Brittingham
Attorney, Agent, or Firm—Kenyon & Kenyon

[57] ABSTRACT

A plastic acetabulum is provided with a plurality of cavities in the outer surface. Each cavity opens conically to the exterior of the acetabulum and the cavities are disposed in concentric rows about the axis of the acetabulum. The cavities are provided with a roughly fixed ratio of depth (t) to width (w) with the volume (v), depth (t) and width (w) decreasing from an edge of the acetabulum to a peak of the acetabulum. The depth and width of the cavities each decrease exponentially in proportion to the ratio of the diametric spacings of the cavity rows. Likewise, the volume of the cavities decrease exponentially from row-to-row in the direction of the peak of the acetabulum.

13 Claims, 1 Drawing Sheet

PLASTIC ACETABULUM

This invention relates to a plastic acetabulum. More particularly, this invention relates to a plastic acetabulum which can be cemented into position.

As is known, various types of acetabula have been known for implantation in a hip joint. In some cases the acetabula have been constructed for cement-less implantation while in other cases, the acetabula have been implanted in a bed of bone cement. For example, U.S. Pat. No. 3,740,769 describes a metal acetabulum which is provided with recesses spaced around the surface of the acetabulum so that bone can grow into the recesses and firmly anchor the acetabulum in place.

U.S Pat. No. 3,806,960 describes an acetabulum which can be cemented into position and which consists of a metal shell which is coated on the outside with a resilient silicone rubber having various grooves and recesses provided therein.

Still other examples of acetabula having various grooves and recesses in an outer surface can be found in Swiss Patent 649,913 as well as in published French Patent Application 7,134,170 and 2,250,279.

Examples of attaching a shaft of a hip joint prosthesis which is surrounded on all sides by means of bone cement with the use of cavities in the shaft can be found in Swiss Patent 666,611.

One problem which arises when securing an acetabulum with bone cement is that the outer shell surface which generally has a shape similar to a hemisphere only offers limited possibilities for securing bone cement which is sensitive to tensile stresses.

Accordingly, it is an object of the invention to provide an acetabulum for securement in a bone cement bed which is not sensitive to tensile stresses.

It is another object of the invention to produce a good attachment between an acetabulum made of plastic and a bone cement bed.

Briefly, the invention provides an acetabulum which is comprised of a non-deformable plastic shell having a hemispherical socket and a plurality of cavities disposed in an outer surface of the shell for receiving bone cement.

In accordance with the invention, each cavity of the acetabulum opens conically to the exterior of the shell. In addition, the cavities have a fixed ratio of depth to width with the volume, depth and width of the cavities decreasing from an edge of the shell in a direction towards a peak (pole) of the shell.

It is to be noted that the ratio of the depth to width of the cavities is described as being a fixed ratio. However, it is to be noted that this is a roughly fixed ratio so that small variations can be accommodated without departing from the scope of the invention.

The advantage of the sizing and pattern of the cavities is that bone cement is permitted to harden in shapes which permit a large transfer of forces to the entire acetabulum with low stress peaks in the bone cement.

These and other objects and advantages of the invention will become more apparent from the following detailed description taken in conjunction with the accompanying drawings wherein.

Figure 1:
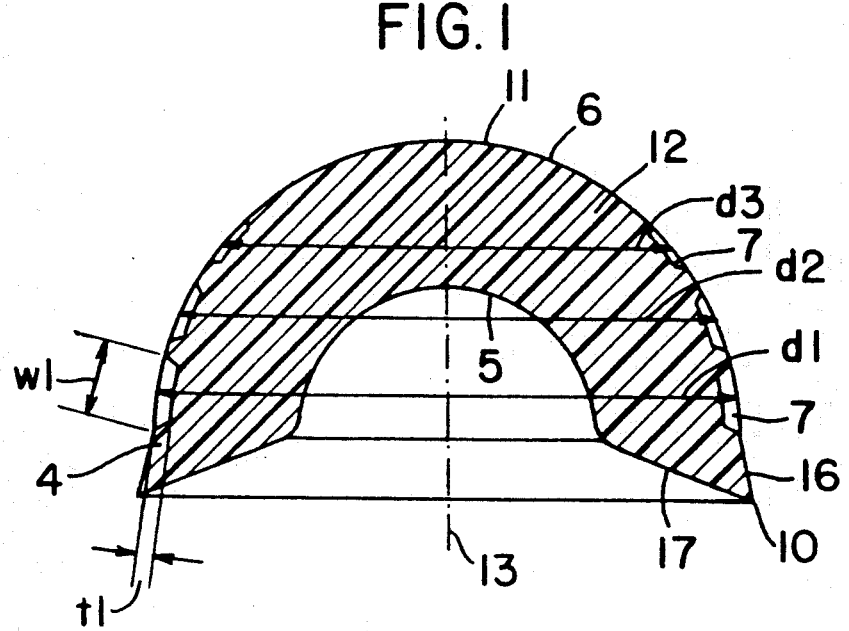
FIG. 1 illustrates a cross-sectional view of an acetabulum constructed in accordance with the invention.

Referring to FIG. 1, the acetabulum 4 is made of a non-deformable plastic shell 12 having a hemispherical socket 5 and a hemispherical outer surface 6. The acetabulum 4 is made, for example of polyethylene, and is to be cemented into position by means of a suitable bone cement.

As illustrated, the acetabulum 4 also has an inner conical surface 17 adjacent to the socket 5 as well as an outer conical surface 16 which merges at a peripheral edge 10 with the conical surface 17. As further indicated, the shell 12 is symmetrical about a central axis 13.

Figure 2:
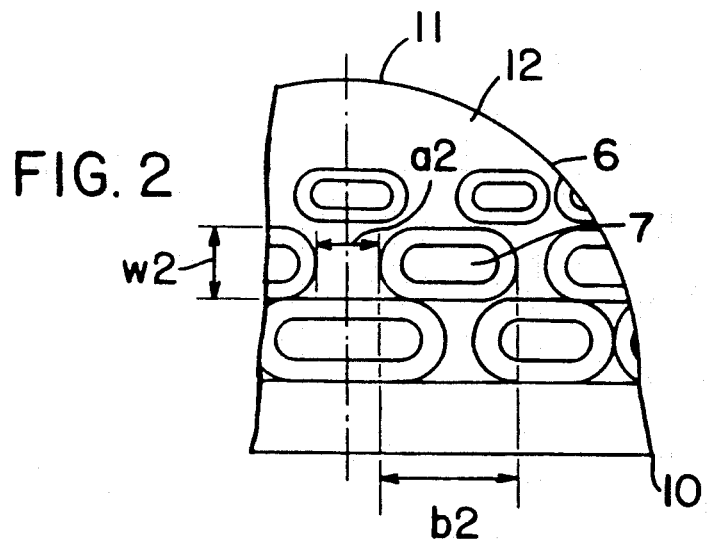
FIG. 2 illustrates a detail of a lateral elevation of the acetabulum according to FIG. 1.
Figure 3:
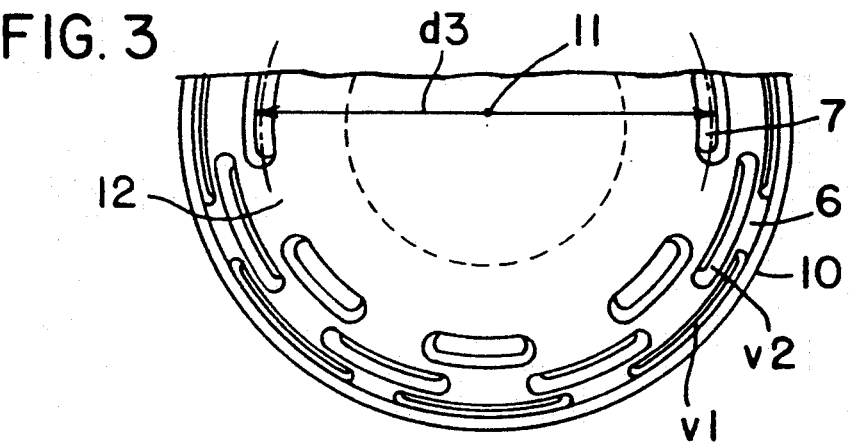
FIG. 3 shows a detail of a plan view of the acetabulum of FIG. 1.

In addition, the shell 12 is provided with a plurality of cavities 7 which are disposed in the outer surface 6 for receiving bone cement. As indicated in FIGS. 2 and 3, the cavities 7 are disposed in concentric rows in the outer surface 6 with each row being in a plane perpendicular to the central axis 13 of the shell 12. As such, the cavities 7 are disposed on different diameters d1, d2, d3 perpendicular to the shell axis 13.

Referring to FIG. 1, each cavity 7 opens conically to the exterior of the shell and has a fixed ratio of depth (t) to width (w) with the volume (v), depth (t) and width (w) of the cavities 7 decreasing from the edge 10 of the shell in a direction towards a peak 11 of the shell. For example, the cavities 7 have a fixed ratio B of their radial depth (t) to the tangential width (w), with B corresponding to a value between 0.10 and 0.5, e.g.

$$\frac{t1}{w1} = 0.2.$$

The depth (t) and the width (w) of two cavities 7 having different diameter spacings d1 and d2 perpendicular to the shell axis 13 decrease exponentially with an exponent α in proportion to the ratio of their diameter spacings d2, d1 perpendicular to the shell axis 13 with the exponent α having a value of between 1.2 and 1.6, e.g.

$$\frac{w2}{w1} = \left(\frac{d2}{d2}\right)^{1.4}$$

The volumes of the cavities also decrease exponentially with an exponent δ in proportion to the diameters in the direction of the peak 11 of the shell 12 with the exponent δ for the diameter ratio d2/d1 assuming a value of between 3.4 and 4.2, e.g.

$$\frac{V2}{V1} = \left(\frac{d2}{d1}\right)^{3.8}.$$

The cavities 7 lying on a common diameter spacing perpendicular to the shell axis 13, i.e. cavities 7 in the same row, have the same dimensions and over the common shell periphery have a smaller spacing a (see FIG. 2) with respect to one another than the cavity breadth b, e.g. a2<b2.

The cavities 7 lying on a common diameter spacing are also staggered over the periphery relative to the cavities 7 of the directly adjacent row (see FIG. 3). The number of cavities is the same from row to row.

The exponents and factors specifying the cavities are chosen so that, firstly, the tensile stresses occurring in the bone cement are not too great when the acetabulum is stressed, and, secondly, when inserting the acetabulum all the cavities are completely filled with bone cement before the cement hardens.

What is claimed is:

1. An acetabulum comprising
a non-deformable plastic shell having a hemispherical socket having a bottom edge and an opposite peak; and
a plurality of cavities disposed in an outer surface of said shell for receiving bone cement, each said cavity opening conically to the exterior of said shell, said cavities having a fixed ratio of depth (t) to width (w) with each of volume (v), depth (t) and width (w) of said cavities decreasing from said bottom edge of said shell in a direction towards said peak of said shell.

2. An acetabulum as set forth in claim 1 wherein said shell is made of polyethylene.

3. An acetabulum as set forth in claim 1 wherein said ratio of depth (t) to width (w) is in a range of from 0.1 to 0.5.

4. An acetabulum as set forth in claim 1 wherein the width (w) and depth (t) of said cavities each decrease exponentially in a range of from 1.2 to 1.6 in proportion to the ratio of the diameter spacings (d) of said cavities taken at right angles to the axis of said shell.

5. An acetabulum as set forth in claim 1 wherein the volume (v) of said cavities decrease exponentially in a range of from 3.4 to 4.2 in proportion to the ratio of the diameter spacings (d) of said cavities taken at right angles to the axis of said shell.

6. An acetabulum as set forth in claim 1 wherein said cavities are disposed in concentric rows over said shell and are equi-spaced in each row.

7. An acetabulum as set forth in claim 6 wherein the number of cavities in each row is equal to the number of cavities in the other rows.

8. An acetabulum as set forth in claim 6 wherein said cavities are staggered relative to each other from row to row.

9. An acetabulum as set forth in claim 6 wherein each cavity in a respective row is of greater breadth (b) than the spacing between adjacent cavities in said respective row.

10. An acetabulum as set forth in claim 1 wherein said cavities are disposed in concentric rows over said shell.

11. An acetabulum as set forth in claim 10 wherein said ratio of depth (t) to width (w) is in a range of from 0.1 to 0.5 and wherein the width (w) of said cavities of each respective row decreases exponentially in proportion to the ratio of the diameter spacings (d) of respective rows relative to an axis of said shell.

12. An acetabulum as set forth in claim 11 wherein said width (w) decreases exponentially in a range of from 1.2 to 1.6 relative to the ratio of diameter spacings of respective rows.

13. An acetabulum as set forth in claim 11 wherein the volume (v) of said cavities decrease exponentially in a range of from 3.4 to 4.2 relative to the ratio of diameter spacings of respective rows.

* * * * *